(12) United States Patent
Tsai et al.

(10) Patent No.: US 10,170,228 B2
(45) Date of Patent: Jan. 1, 2019

(54) MAGNETIC APPARATUS

(71) Applicant: NATIONAL SYNCHROTRON RADIATION RESEARCH CENTER, Hsinchu (TW)

(72) Inventors: Kuang-Lung Tsai, Hsinchu (TW); Chyi-Shyan Fann, Hsinchu (TW); Ching-Lung Chen, Hsinchu (TW); Ho-Ping Chang, Hsinchu (TW); Ke-Kang Lin, Hsinchu (TW)

(73) Assignee: NATIONAL SYNCHROTRON RADIATION RESEARCH CENTER, Hsinchu (TW)

( * ) Notice: Subject to any disclaimer, the term of this patent is extended or adjusted under 35 U.S.C. 154(b) by 0 days.

(21) Appl. No.: 15/403,697

(22) Filed: Jan. 11, 2017

(65) Prior Publication Data

US 2018/0197667 A1    Jul. 12, 2018

(51) Int. Cl.
*H01F 7/20* (2006.01)
*A61N 5/10* (2006.01)

(52) U.S. Cl.
CPC ............. *H01F 7/202* (2013.01); *A61N 5/10* (2013.01); *A61N 2005/1095* (2013.01)

(58) Field of Classification Search
CPC ... H01F 7/00; H01F 7/02; H01F 7/021; H01F 7/0221; H01F 7/06; H01F 7/062; H01F 7/08; H01F 7/081; H01F 7/086; H01F 7/121; H01F 7/126; H01F 7/129; H01F 7/14; H01F 7/16; H01F 7/202; A61N 5/10; H01J 37/00; H01J 37/02; H01J 37/10; H01J 37/14; H01J 37/141; H01J 37/1413; H01J 37/143; H01J 37/145; H01J 37/147; H01J 37/1472

USPC .............. 250/306, 307, 311, 396 R, 396 ML
See application file for complete search history.

(56) References Cited

U.S. PATENT DOCUMENTS

| | | | | |
|---|---|---|---|---|
| 4,075,488 A | * | 2/1978 | Okayama | H01J 37/3007 250/396 R |
| 4,429,229 A | * | 1/1984 | Gluckstern | G21K 1/093 250/396 ML |
| 5,221,844 A | * | 6/1993 | van der Mast | H01J 37/153 250/396 ML |
| 6,441,382 B1 | | 8/2002 | Huang | |

(Continued)

FOREIGN PATENT DOCUMENTS

| | | |
|---|---|---|
| TW | 201318660 A | 5/2013 |
| TW | I466157 B | 12/2014 |

(Continued)

OTHER PUBLICATIONS

Office Action dated Nov. 28, 2017 in TW Application No. 106114467 (3 pages).

*Primary Examiner* — Jason McCormack
(74) *Attorney, Agent, or Firm* — Muncy, Geissler, Olds. & Lowe, P.C.

(57) ABSTRACT

A magnetic apparatus includes a first conductive feature. The first conductive feature conducts a current. The first conductive feature directs an electron having an energy ranging from 50 to 250 MeV in response to a magnetic field generated by the current. The first conductive feature includes a first leg and a second leg. The first leg is integrated with the second leg. The second leg and the first leg define a first space, wherein the electron penetrates the first space and is redirected in the first space.

21 Claims, 12 Drawing Sheets

(56) References Cited

U.S. PATENT DOCUMENTS

| | | | |
|---|---|---|---|
| 7,718,980 B2 | 5/2010 | Tsukihara et al. | |
| 8,436,317 B1 * | 5/2013 | Chen | H01J 37/05 250/396 ML |
| 8,618,521 B2 | 12/2013 | Loo et al. | |
| 2014/0158901 A1 * | 6/2014 | Sawada | H01J 37/153 250/396 R |
| 2015/0129772 A1 * | 5/2015 | Candler | H05H 7/04 250/396 ML |
| 2016/0042911 A1 * | 2/2016 | Chang | H01J 37/145 250/311 |

FOREIGN PATENT DOCUMENTS

| | | |
|---|---|---|
| TW | 201609216 A | 3/2016 |
| TW | 201609218 A | 3/2016 |

* cited by examiner

MAGNETIC APPARATUS

TECHNICAL FIELD

The present disclosure relates to a magnetic apparatus, and more particularly, to a magnetic apparatus for directing an electron with very high energy to treat a patient.

DISCUSSION OF THE BACKGROUND

Among radiation therapies, the method of cancer treatment using linear energy transfer (LET) radiation, including neutron or baryon beams, enables minimization of the exposure of healthy tissues to radiation intended for cancer cells, and focuses the therapeutic amount of radiation to cancerous cells only. Thus, radiation therapy that uses high-LET radiation is recognized as being far more effective than radiation therapy that uses low-LET radiation. High-LET radiation includes electrons, alpha-ray, neutron-ray, and baryon-ray.

This Discussion of the Background section is provided for background information only. The statements in this Discussion of the Background are not an admission that the subject matter disclosed in this section constitutes prior art to the present disclosure, and no part of this section may be used as an admission that any part of this application, including this Discussion of the Background section, constitutes prior art to the present disclosure.

SUMMARY

One aspect of the present disclosure provides a magnetic apparatus. The magnetic apparatus includes a first conductive feature. The first conductive feature conducts a current. The first conductive feature directs an electron having an energy ranging from 50 to 250 MeV as the electron passes through a magnetic field generated by the current. The first conductive feature includes a first leg and a second leg. The first leg is integrated with the second leg in the first conductive feature while separate from the second leg. The second leg and the first leg define a first space, wherein the electron penetrates the first space and is directed in the first space.

In some embodiments, the current is in a half-sinewave form.

In some embodiments, the first leg is parallel to the second leg.

In some embodiments, the first leg is not parallel to the second leg.

In some embodiments, the magnetic apparatus further includes a first frame configured to connect the first leg to the second leg, wherein the first frame has a second space therein, which is connected to the first space, and the electron penetrates the second space.

In some embodiments, the first conductive feature includes a coil.

In some embodiments, the coil includes a single-turn coil.

In some embodiments, the first leg has a length of 74 cm, which is substantially equal to a distance in the first space at which the electron is directed.

In some embodiments, the first conductive feature is rotatable. The magnetic apparatus further includes a rotation feature configured to rotate the first conductive feature either clockwise or counterclockwise.

In some embodiments, the rotation feature includes a gantry.

Another aspect of the present disclosure provides a magnetic apparatus. The magnetic apparatus includes a first conductive feature and a second conductive feature. The first conductive feature is configured to generate a first magnetic field. The first conductive feature includes a first leg and a second leg. The first leg is integrated with the second leg in the first conductive feature while separate from the second leg. The second conductive feature is configured to generate a second magnetic field. A direction of the second magnetic field is different from that of the first magnetic field. The first conductive feature and the second conductive feature, electrically isolated from each other, are configured to direct an electron having an energy ranging from 50 to 250 MeV. The second conductive feature includes a third leg and a fourth leg. The first leg, the second leg, the third leg and the fourth leg together define a first space, wherein the electron penetrates the first space and is directed in the first space. The third leg is integrated with the fourth leg in the second conductive feature while separate from the fourth leg.

In some embodiments, the first leg is parallel to the second leg, and the third leg is parallel to the fourth leg.

In some embodiments, the first leg is not parallel to the second leg, and the third leg is not parallel to the fourth leg.

In some embodiments, the first conductive feature further includes a first frame having a second space therein, wherein the first frame is configured to connect the first leg to the second leg. The second conductive feature includes a second frame having a third space therein, wherein the second frame is opposed to the first frame, and the second frame is configured to connect the third leg to the fourth leg, wherein the first space, the second space and the third space are connected to each other.

In some embodiments, each of the first conductive feature and the second conductive feature is configured to conduct a current. The first conductive feature generates the first magnetic field in response to the current, and the second conductive feature generates the second magnetic field in response to the current.

In some embodiments, the current is in a half-sinewave form.

In some embodiments, each of the first conductive feature and the second conductive feature includes a coil.

In some embodiments, the coil includes a single-turn coil.

In some embodiments, each of the first leg and the third leg has a length of 74 cm, which is substantially equal to a distance in the first space at which the electron is directed.

In some embodiments, a plane where the first leg and the second leg are arranged is perpendicular to a plane where the third leg and the fourth leg are arranged.

In some embodiments, a plane where the first leg and the second leg are arranged is not perpendicular to a plane where the third leg and the fourth leg are arranged.

In some embodiments, the first conductive feature further includes a first frame having a second space therein, wherein the first frame is configured to connect the first leg to the second leg. The second conductive feature includes a second frame having a third space therein, wherein the second frame overlaps the first frame, and wherein the second frame is configured to connect the third leg to the fourth leg, wherein the first space, the second space and the third space are connected to each other.

In some embodiments, the first conductive feature further includes a first frame having a second space therein. The first frame is configured to connect the first leg to the second leg. The second conductive feature includes a second frame having a third space therein, and is configured to connect the third leg to the fourth leg. The second space and the third space are at the same side of the first space.

In some embodiments, the first leg and the second leg are alternately connected to a first node and a second node of a current source.

In some embodiments, a rotation feature configured to rotate the first conductive feature and the second conductive feature either clockwise or counterclockwise In some related magnetic apparatus, a current with a pulse form (or called a pulsating direct current) is generated and provided to a conductive feature (such as a coil), such that the conductive feature generates a magnetic field to direct an electron having an energy ranging from 50 to 250 MeV. To direct such electron, such that the electron is redirected from its original direction by a relatively large angle, a relatively high magnitude of pulsating current is required. However, pulsating current generally has a relatively low magnitude due to the difficulty in generating high-magnitude pulsating currents. Such resulting low-magnitude pulsating current is only able to redirect the electron by a relatively small angle. To achieve a distance of deviation in an x-axis, a relatively long leg of the conductive feature is required. Consequently, the conductive feature would need to be relatively large.

In contrast, in the present disclosure, a current flowing into a conductive feature has a half-sinewave form and a peak magnitude of the half sinewave is greater than or equal to about, for example, 8000 A (Ampere), wherein a magnitude of 8000 A is a relatively high magnitude. Such resulting high-magnitude current is able to redirect the electron by a relatively large angle. To achieve the same distance of deviation in an x-axis as previously discussed a relatively short leg of the conductive feature is required. Therefore, the size of the conductive feature is relatively small.

Moreover, in the present disclosure, due to the structural arrangement of a first conductive feature and a second conductive feature, an electron can be directed by the simultaneous influence of a first magnetic field and a second magnetic field. Therefore, it is not necessary to have a relatively larger width in an x-axis, for example larger than a width of a first space defined by the first conductive structure and the second conductive structure, to allow sufficient space in an x-axis for the electron to be redirected the desired distance in a z-axis. Accordingly, the width in an x-axis can remain relatively small, allowing the size of a housing containing the first conductive feature and the second conductive feature to also be relatively small. Moreover, in an embodiment, each of the first conductive feature and the second conductive feature can conduct a current with a half-sinewave form, wherein a peak magnitude of the half sinewave is greater than or equal to about, for example, 8000 A. As mentioned above, the length of each of the first conductive feature and the second conductive feature are both relatively short. In this case, the length and the width are both relatively short, and therefore the size of a housing containing the first conductive feature and the second conductive feature is relatively small.

In some related magnetic apparatuses, a first conductive feature and a second conductive feature are separate from each other, and arranged in order in a y-axis. The first conductive feature functions to direct an electron in an x-axis, and the second conductive feature functions to direct the electron in a z-axis. In operation, although the electron leaves from a space defined by the first conductive feature, and enters a space defined by the second conductive feature and therefore the electron is no longer redirected by an magnetic field generated by the first conductive feature, the electron, in the space defined by the second conductive feature, still moves in an x-axis. Because a position in an x-axis is out of a housing, the electron may strike a wall, in an x-axis, of the housing. To ensure proper direction of the electron, therefore, it would require increasing a size of the housing. For example, the housing is enlarged to another housing. Therefore, a size of a housing containing the first conductive feature and the second conductive feature separate from each other need to be relatively large.

In contrast, in the present disclosure, since the first conductive feature and the second conductive feature together define a space in which the electron is redirected, the size of the housing containing the first conductive feature and the second conductive feature is relatively small.

The foregoing has outlined rather broadly the features and technical advantages of the present disclosure in order that the detailed description of the disclosure that follows may be better understood. Additional features and advantages of the disclosure are described hereinafter, and form the subject of the claims of the disclosure. It should be appreciated by those skilled in the art that the conception and specific embodiment disclosed may be readily utilized as a basis for modifying or designing other structures or processes for carrying out the same purposes of the present disclosure. It should also be realized by those skilled in the art that such equivalent constructions do not depart from the spirit and scope of the disclosure as set forth in the appended claims.

BRIEF DESCRIPTION OF THE DRAWINGS

A more complete understanding of the present disclosure may be derived by referring to the detailed description and claims when considered in connection with the Figures, where like reference numbers refer to similar elements throughout the Figures, and:

DETAILED DESCRIPTION

Figure 1:
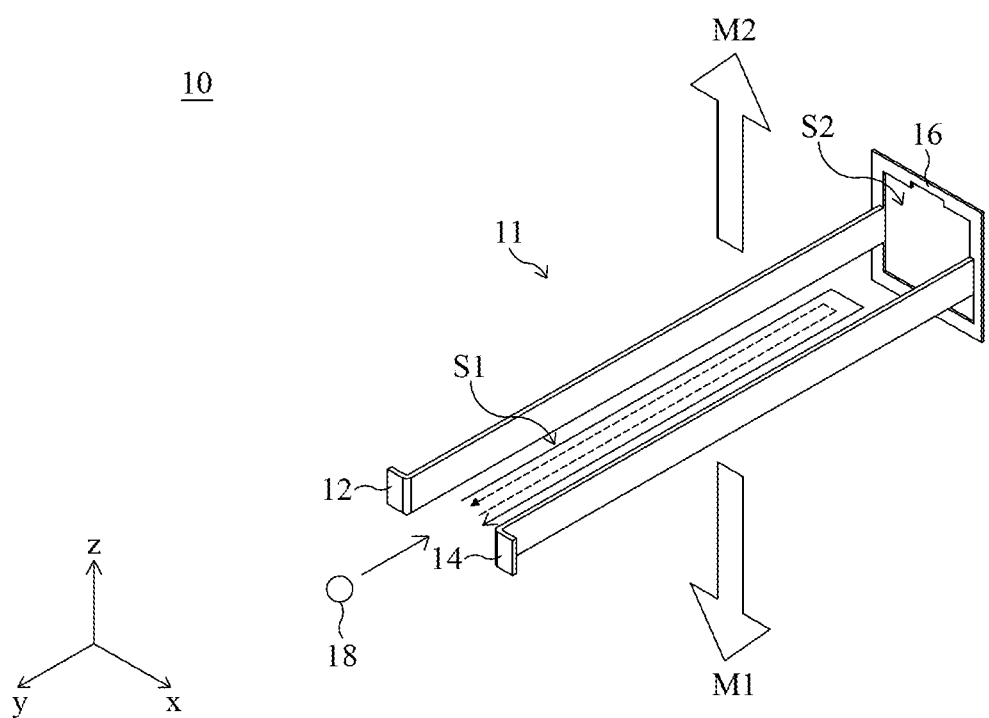
FIG. 1 is a diagram illustrating an action of an electron with a very high energy in a magnetic apparatus in accordance with some embodiments of the present disclosure.

Embodiments, or examples, of the disclosure illustrated in the drawings are now described using specific language. It shall be understood that no limitation of the scope of the disclosure is thereby intended. Any alteration or modification to the described embodiments, and any further applications of principles described in this document, are to be considered as normally occurring to one of ordinary skill in the art to which the disclosure relates. Reference numerals may be repeated throughout the embodiments, but this does not necessarily require that feature(s) of one embodiment apply to another embodiment, even if they share the same reference numeral.

It shall be understood that when an element is referred to as being "connected to" or "coupled with" another element, it may be directly connected to or coupled to the other element, or intervening elements may be present.

It shall be understood that, although the terms first, second, third, etc. may be used herein to describe various elements, components, regions, layers or sections, these elements, components, regions, layers or sections should not be limited by these terms. Rather, these terms are merely used to distinguish one element, component, region, layer or section from another region, layer or section. Thus, a first element, component, region, layer or section discussed below could be termed a second element, component, region, layer or section without departing from the teachings of the present inventive concept.

The terminology used herein is for the purpose of describing particular example embodiments only and is not intended to be limiting of the present inventive concept. As used herein, the singular forms "a," "an" and "the" are intended to include the plural forms as well, unless the context clearly indicates otherwise. It shall be further understood that the terms "comprises" and "comprising," when used in this specification, specify the presence of stated features, integers, steps, operations, elements, or components, but do not preclude the presence or addition of one or more other features, integers, steps, operations, elements, components, or groups thereof.

FIG. 1 is a diagram illustrating an action of an electron 18 with a very high energy in a magnetic apparatus 10 in accordance with some embodiments of the present disclosure. Referring to FIG. 1, the magnetic apparatus 10 for treating a patient includes a first conductive feature 11 including a first leg 12 extending along a direction such as a y-axis, a second leg 14 extending along a direction such as a y-axis and a first body 16.

The first conductive feature 11 functions to conduct a current. In an embodiment, the current is in a half-sinewave form. The current is provided by a current source (not shown), which may be integrated in or external to the magnetic apparatus 10. The current source may determine a flowing direction of the current, allowing the current to generate different directions of magnetic field. In further detail, the current is able to flow from the first leg 12 through the first body 16 to the second leg 14 as indicated in FIG. 1 by a solid-line arrow. The direction of a magnetic force is denoted by M1. Alternatively, the current is able to flow from the second leg 14 through the first body 16 to the first leg 12 as indicated in FIG. 1 by a dashed-line arrow. The direction of magnetic force is denoted by M2.

Figure 2:
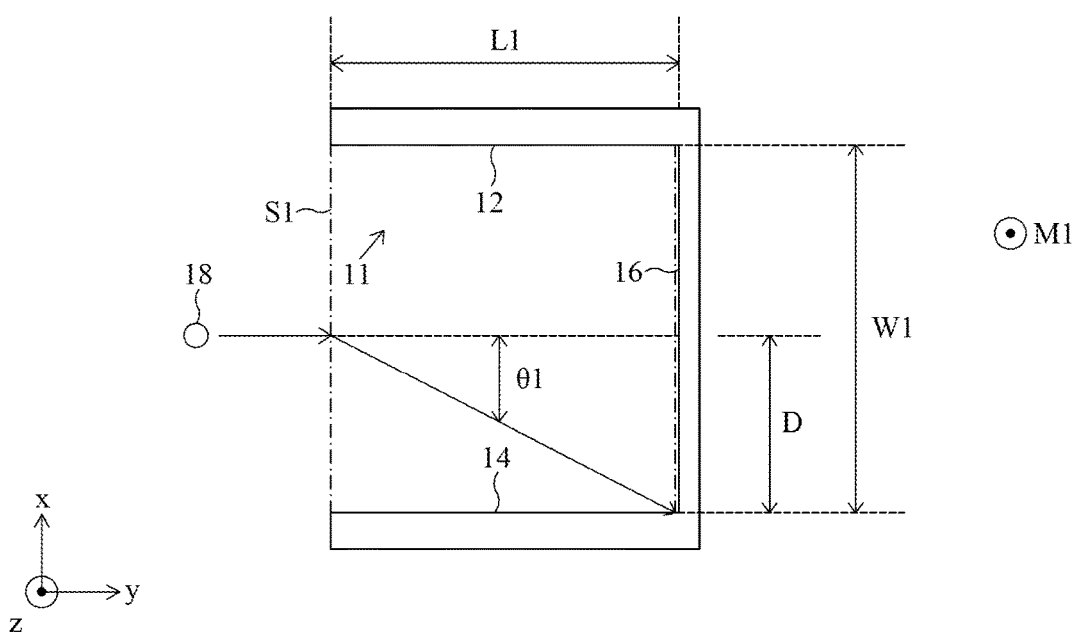
FIG. 2 is a top view of the magnetic apparatus of FIG. 1 in accordance with some embodiments of the present disclosure.

The first conductive feature 11 functions to direct the electron 18 having an energy ranging from 50 to 250 MeV (electron volt) as the electron passes through a magnetic field generated by the current, as illustrated in FIG. 2. In an embodiment, the first conductive feature 11 includes a coil. In another embodiment, the first conductive feature 11 includes a single-turn coil.

The first leg 12 and the second leg 14 are integrated together, and define a first space S1 therebetween. In further detail, the first leg 12 is integrated with the second leg 14 in the first conductive feature 11 (i.e., each of the first leg 12 and the second leg 14 is a part of the first conductive feature 11). The electron 18 penetrates the first space S1 and is redirected as the electron 18 passes through the first space S1. In an embodiment, the first leg 12 is parallel to the second leg 14. In another embodiment, the first leg 12 is not parallel to the second leg 14. Moreover, in practice, a distance in an x-axis between the first leg 12 and the second leg 14 is extremely short, which means that the first leg 12 is very close to the second leg 14.

The first body 16 functions to connect the first leg 12 to the second leg 14. The first body 16 has a first side and a second side opposite to the first side. In an embodiment, the first leg 12 is disposed at the first side, and the second leg 14 is disposed at the second side. The first body 16 has a second space S2 therein. The second space S2 is connected to the first space S1. The electron 18 penetrates the second space S2, wherein the electron 18 may not be redirected in the second space S2.

In an embodiment, a cross-sectional shape of the first body 16 includes a frame. Alternatively, other cross-sectional shapes of the first body 16 may comprise circles, ellipses, ellipsoids, ovoids, regular polygons (e.g., equilateral triangles, regular pentagons, regular hexagons, stars, etc., including other regular polygons of any order of rotational symmetry greater than three), irregular polygons (e.g., isosceles triangles, scalene triangles, rectangles, trapezoids, rhomboids, etc., including other irregular polygons having any number of sides greater than three), or combinations thereof. Any cross-sectional shape may generally be represented by superimpositions or discrete combinations of the aforementioned shapes. Accordingly, representative embodiments of the first body 16 disclosed herein are not limited to any particular cross-sectional shape.

FIG. 2 is a top view of the magnetic apparatus 10 of FIG. 1 in accordance with some embodiments of the present disclosure. Referring to FIG. 2, because the peak of the current is higher than or equal to about (i.e., at least), for example, 8000 A, the first conductive feature 11 is able to redirect the electron 18, such that the electron 18 is redirected from its original direction by an angle $\theta_1$, which is a relatively large angle. The angle $\theta_1$ may be, for example, 6 degrees. As a result, in a limited distance in a y-axis, the electron 18 is still able to move a desired distance D in an x-axis. It should be noted that the straight line shown in FIG. 2 does not refer to a path trace along which the electron 18 moves. Accordingly, it is not necessary to increase a length L1 in a y-axis of the first leg 12 (and the second leg 14), and therefore the length L1 in a y-axis of the first leg 12 is relatively short. The length L1 can be deemed as a length in a y-axis of the first conductive feature 11. Therefore, the size of the first conductive feature 11 is relatively small. In an embodiment, the first leg 12 and the second leg 14 each has a length of about 74 cm, which is relatively short. The length of about 74 cm is substantially equal to a distance, in the first space S1, at which the electron 18 is redirected. Moreover, the length of about 74 cm reflects a fact that the first conductive feature 11 conducts a current with a half-sinewave form and a peak magnitude of the half sinewave is equal to or greater than, for example, 8000 A. In the present embodiment, as depicted in FIG. 2, since a magnetic field is the magnetic field M1, the electron 18 is forced to move toward the second leg 14. In contrast, if a magnetic field is the magnetic field M2, the electron is forced to move toward the first leg 12.

Figure 3:
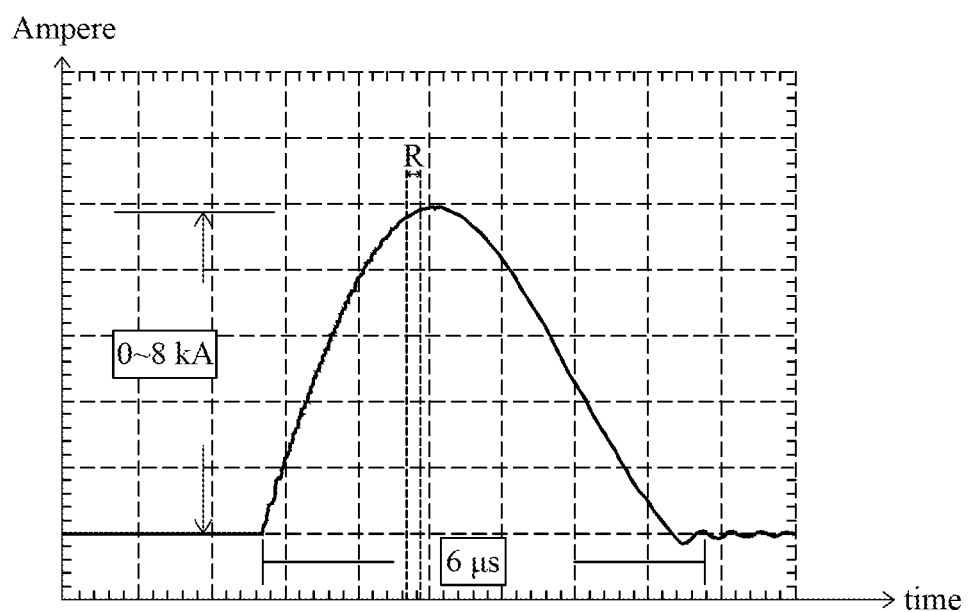
FIG. 3 is a schematic diagram showing measurement results of the current flowing into the first conductive feature of FIG. 1 in accordance with some embodiments of the present disclosure.

FIG. 3 is a schematic diagram showing measurement results of the current flowing into the first conductive feature 11 of FIG. 1 in accordance with some embodiments of the present disclosure. Referring to FIG. 3, a horizontal axis represents a time and a vertical axis represents a magnitude (in amperes) of the current flowing into the first conductive feature 11. As illustrated in FIG. 3, a peak magnitude of the half sinewave is greater than or equal to about, for example, 8000 A. A timing for emitting the electron 18 can be determined. In further detail, when the magnitude of the current substantially achieves the peak magnitude of about 8000 A (for example, during a period of time R in FIG. 3), the electron 18 is emitted into the first space S1 defined by the first conductive feature 11. As such, for the electron 18, the current is deemed as a pulse (i.e., deemed as a pulse of a pulsating direct current). The pulse of about 8000 A is relatively high. The electron 18 can therefore be redirected by a relatively large degree, about 6 degrees.

Figure 4:
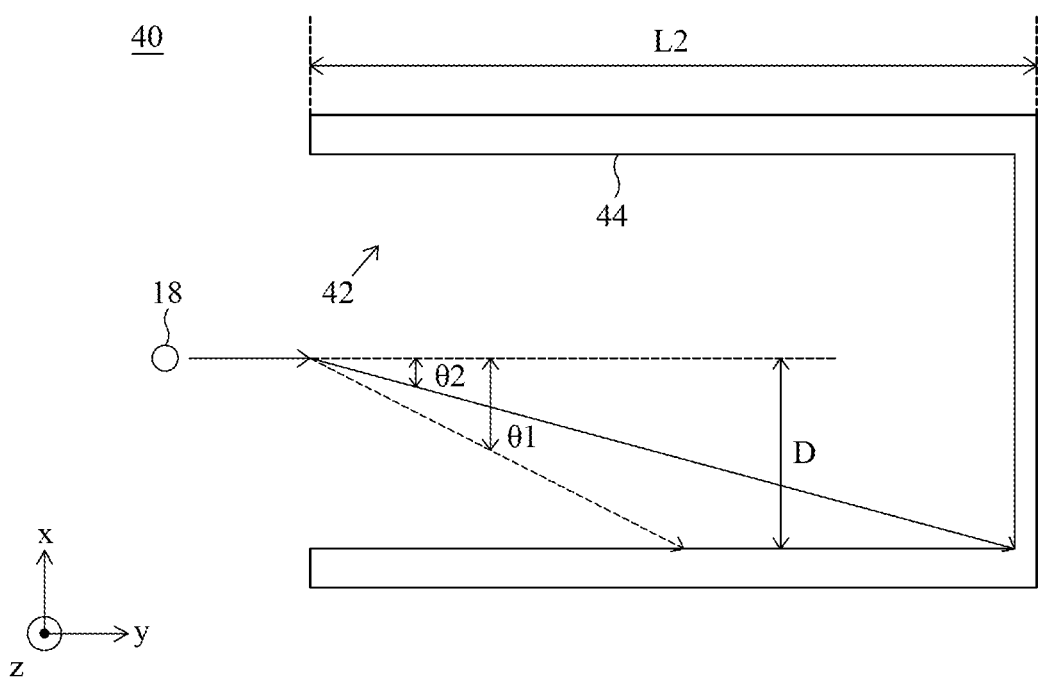
FIG. 4 is a schematic diagram of a magnetic apparatus in a related art.

FIG. 4 is a schematic diagram of a magnetic apparatus 40 in a related art. Referring to FIG. 4, the magnetic apparatus 40 includes a conductive feature 42 including a leg 44. A pulsating direct current is generated and provided to the conductive feature 42, such that the conductive feature 42 generates a magnetic field to redirect an electron 18. To redirect an electron having an energy ranging from 50 to 250 MeV, such that the electron is redirected from its original direction by a relatively large angle, a relatively high magnitude of pulsating direct current is required. However, pulsating direct current generally has a relatively low magnitude due to the difficulty of generating a pulsating direct current having relatively high magnitude. Such resulting low-magnitude pulsating current is only able to redirect the electron 18 from its original direction by a relatively small angle θ2, which is less than the angle θ1. To achieve the same distance D in an x-axis, a relatively large length L2, greater than the length L1, of the leg 44 of the conductive feature 42 is required. Consequently, the size of the conductive feature 42 is relatively large. As a result, the size of a housing containing the conductive feature 42 is relatively large.

In contrast, in the present disclosure, as mentioned above, a current flowing into the first conductive feature 11 has a half-sinewave form and a peak magnitude of the half sinewave is greater than or equal to about, for example, 8000 A (Ampere), wherein a magnitude of 8000 A is a relatively high magnitude. Such resulting high-magnitude current is able to redirect the electron 18 by a relatively large angle θ1. To achieve the same distance D of deviation in an x-axis as previously discussed a relatively short leg of the conductive feature 11 is provided. Therefore, the size of the conductive feature 11 is relatively small. As a result, the size of a casing containing the conductive feature 11 is relatively small.

Figure 5:
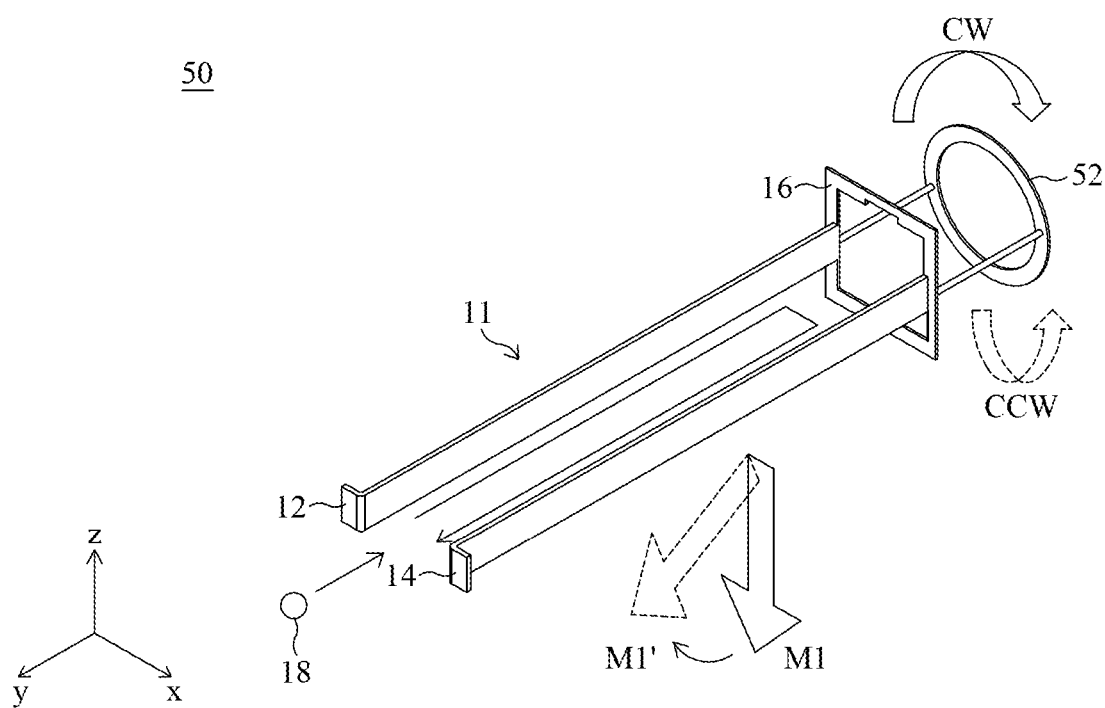
FIG. 5 is a schematic diagram of a magnetic apparatus including the magnetic structure of FIG. 1 in accordance with some embodiments of the present disclosure.

FIG. 5 is a schematic diagram of a magnetic apparatus 50 including the magnetic structure 11 of FIG. 1 in accordance with some embodiments of the present disclosure. Referring to FIG. 5, the magnetic apparatus 50 is similar to the magnetic apparatus 10 described and illustrated with reference to FIG. 1 except that, for example, the magnetic apparatus 50 includes a rotation feature 52 and the first conductive feature 11 is rotatable.

The rotation feature 52 functions to rotate the first conductive feature 11 either clockwise CW or counterclockwise CCW in an x-z plane. In an embodiment, the rotation feature 52 includes a gantry.

In operation, when the first conductive feature 11 rotates, the direction of the magnetic field with respect to the electron 18 accordingly rotates. For example, when the first conductive feature 11 rotates clockwise, the magnetic field M1 is rotated to the magnetic field M1'. With variation in direction of a magnetic field, a direction of a magnetic force varies. Therefore, the electron 18 can be directed in the first conductive feature 11 in all directions (360 degrees) without increasing size of the first conductive feature 11.

Figure 6:
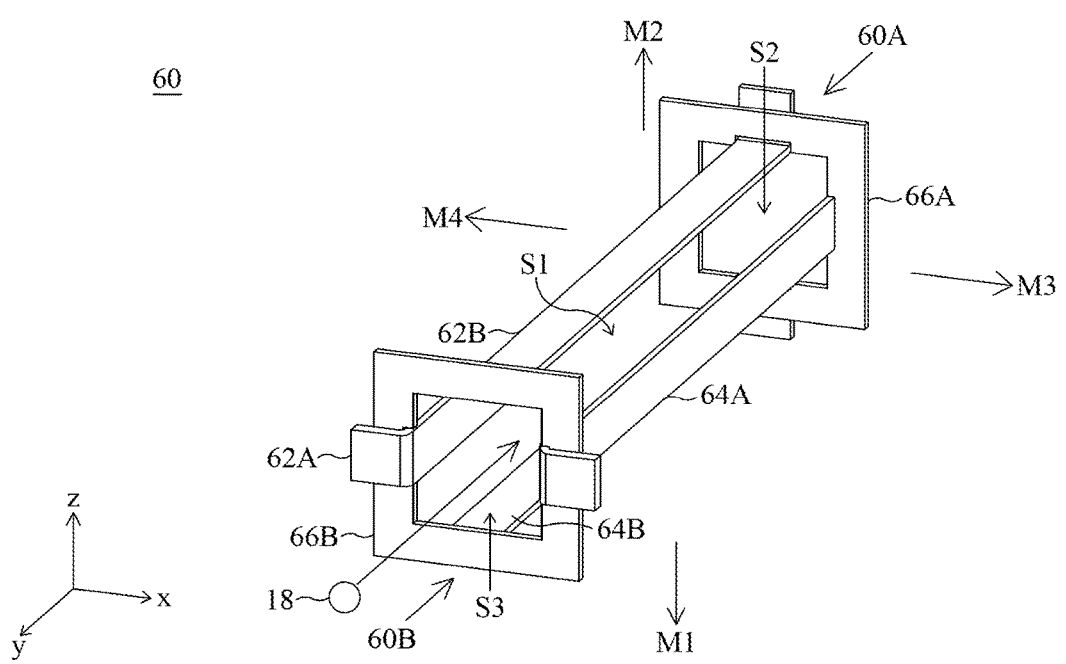
FIG. 6 is a schematic diagram of another magnetic apparatus in accordance with some embodiments of the present disclosure.

FIG. 6 is a schematic diagram of another magnetic apparatus 60 in accordance with some embodiments of the present disclosure. Referring to FIG. 6, the magnetic apparatus 60 includes a first conductive feature 60A and a second conductive feature 60B. Function and structure of each of the first conductive feature 60A and a second conductive feature 60B are the same as those of the first conductive feature 11. As a result, some detailed descriptions are omitted herein. The first conductive feature 60A and the second conductive feature 60B are substantially at the same position in a y-axis.

The first conductive feature 60A and the second conductive feature 60B, electrically isolated from each other, function to redirect an electron having an energy ranging from 50 to 250 MeV as the electron passes through magnetic fields generated by the first conductive feature 60A and the second conductive feature 60B. The first conductive feature 60A functions to generate a first magnetic field in a z-axis. For example, the first magnetic field is the first magnetic field M1, or the first magnetic field M2. The second conductive feature 60B functions to generate a second magnetic field in an x-axis. For example, the second magnetic field is a second magnetic field M3, or a second magnetic field M4.

A first leg 62A and a second leg 64A of the first conductive feature 62 and a third leg 62B and a fourth leg 64B of the second conductive feature 64 together define a first space S1. The third leg 62B is integrated with the fourth leg 64B in the second conductive feature 64 while separate from the fourth leg 64B. That is, both the third leg 62B and the fourth leg 64B are a part of the second conductive feature 64. The electron 18 penetrates the first space S1 and is redirected as it passes through the first space S1. In an embodiment, the first leg 62A is parallel to the second leg 64A, and the third leg 62B is parallel to the fourth leg 64B. In another embodiment, the first leg 62A is not parallel to the second leg 62B, and the third leg 64A is not parallel to the fourth leg 64B.

A first frame 66A of the first conductive feature 60A includes a second space S2 therein. The first frame 66A functions to connect the first leg 62A to the second leg 64A. Similarly, a second frame 66B of the second conductive feature 60B has a third space S3 therein. The second frame 66B is opposed to the first frame 66A, and functions to connect the third leg 62B to the fourth leg 64B. The first space S1, the second space S2 and the third space S3 are connected to each other.

In an embodiment, a current direction of each of the first conductive feature 60A and the second conductive feature 60B can be varied. For example, the first leg 62A and the second leg 64A are alternately connected to a first node and a second node of a current source (not shown). In this way, a magnetic field can be accordingly varied. With variation in direction of a magnetic field, a direction of a magnetic force varies. Therefore, the electron 18 can be directed in the first conductive feature 60A and the second conductive feature 60B in all directions (360 degrees) without increasing size of the first conductive feature 60A and the second conductive feature 60B. Moreover, design of the magnetic apparatus 60 including a first conductive feature 60A and a second conductive feature 60B is relatively simple.

Figure 7:
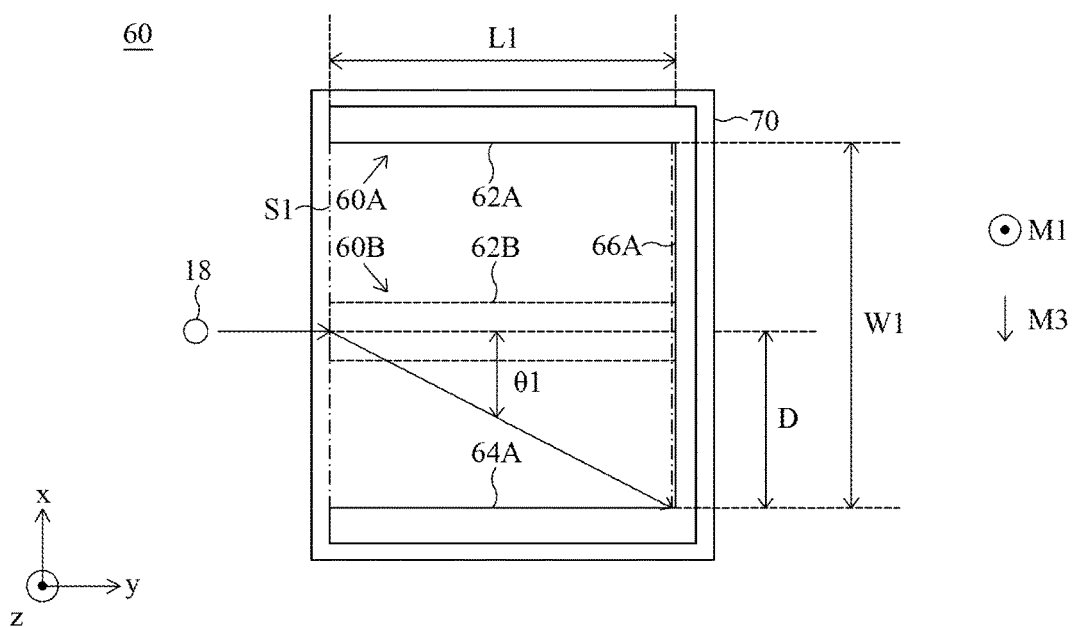
FIG. 7 is a top view of the magnetic apparatus of FIG. 6 in accordance with some embodiments of the present disclosure.

FIG. 7 is a top view of the magnetic apparatus 60 of FIG. 6 in accordance with some embodiments of the present disclosure. For clarity of illustration, the fourth leg 64B and the second frame 66B of the second conductive feature 60B are not shown in FIG. 7. Due to the structural arrangement of the first conductive feature 60A and the second conductive feature 60B, the electron 18 can be directed by the simultaneous influence of the first magnetic field (such as the first magnetic field M1) and the second magnetic field (such as the second magnetic field M3). That is, when the electron 18 is redirected a desired distance in an x-axis, the electron 18 can also be redirected a desired distance in a z-axis simultaneously. Therefore, it is not necessary to have a relatively larger width in an x-axis, for example larger than the width W1 of the first space S1, to allow sufficient space in an x-axis for the electron 18 to be redirected the desired distance in a z-axis, which will be described in detail with reference to FIG. 8. Accordingly, the width W1 in an x-axis can remain relatively small, allowing the size of a housing containing the first conductive feature 60A and the second conductive feature 60B to also be relatively small.

In an embodiment, each of the first conductive feature 60A and the second conductive feature 60B functions to conduct a current with a half-sinewave form. A peak magnitude of the half sinewave is higher than or equal to, for example, 8000 A. As mentioned above, the length L1 of each of the first conductive feature 60A and the second conductive feature 60B is relatively short. The length L1 of each of the first conductive feature 60A and the second conductive feature 60B can be deemed as a length of a housing 70. In this case, both the length L1 and the width W1 are relatively short, and therefore the size of the housing 70 containing the first conductive feature 60A and the second conductive feature 60B is relatively small.

Figure 8:
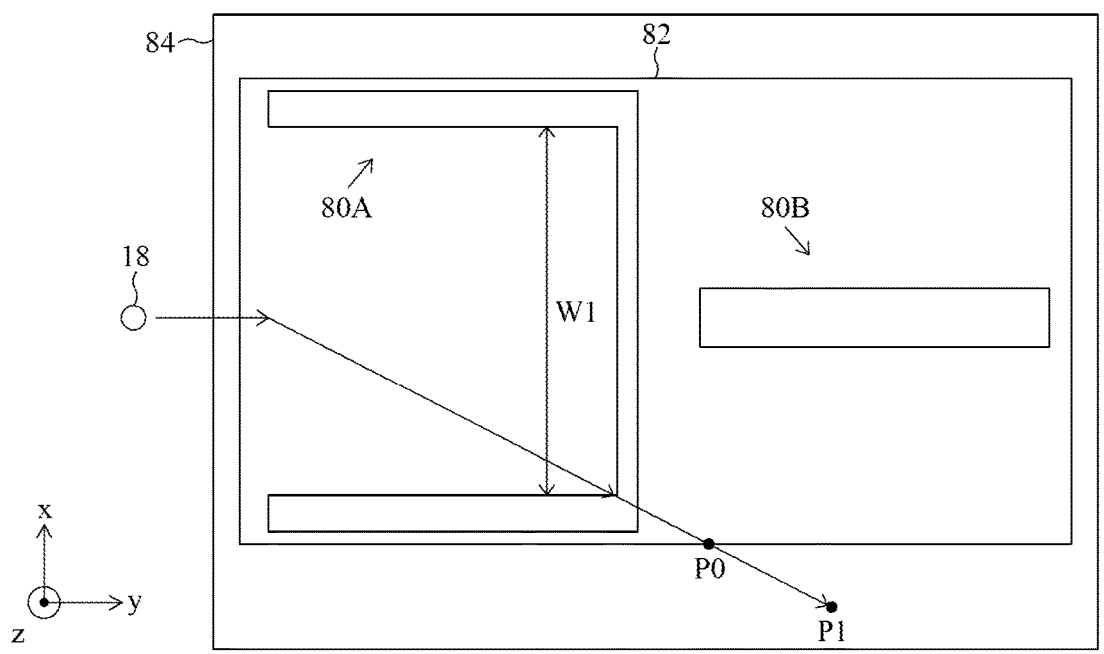
FIG. 8 is a schematic diagram of a magnetic apparatus in a related art.

FIG. 8 is a schematic diagram of a magnetic apparatus 80 in a related art. Referring to FIG. 8, the magnetic apparatus 80 includes a first conductive feature 80A and a second conductive feature 80B. Structure and function of the first conductive feature 80A and the second conductive feature 80B are the same as those of the first conductive feature 60A and the second conductive feature 60B of FIG. 7 except that a structural arrangement between the first conductive feature 80A and the second conductive feature 80B. In further detail, the first conductive feature 80A and the second conductive feature 80B are separate from each other, and arranged in order in a y-axis.

It is assumed that the first conductive feature 80A and the second conductive feature 80B are accommodated in a case 82. The case 82 has the same width W1 as the case 70. Moreover, it is assumed that the electron 18 is redirected to a desired position in a z-axis when the electron 18 achieves a position P1 in an x-axis.

In operation, although the electron 18 leaves from a space defined by the first conductive feature 80A, and enters a space defined by the second conductive feature 80B and therefore the electron 18 is no longer redirected by an magnetic field generated by the first conductive feature 80A, the electron 18, in the space defined by the second conductive feature 80B, still moves in an x-axis. Because the position P1 in an x-axis is out of the housing 82, the electron 18 may strike a wall, in an x-axis, of the housing 82 at a position P0. To ensure proper direction of the electron, therefore, it would require increasing a size of the housing 82. For example, the housing 82 is enlarged to a housing 84 within which the position P1 is. Therefore, a size of the housing 84 containing the first conductive feature 80A and the second conductive feature 80B separate from each other need to be relatively large.

In contrast, in the present disclosure, as mentioned in the description of FIG. 7, since the first conductive feature 60A and the second conductive feature 60B together define a space in which the electron 18 is redirected, the size of the housing 70 containing the first conductive feature 60A and the second conductive feature 60B is relatively small.

Figure 9:
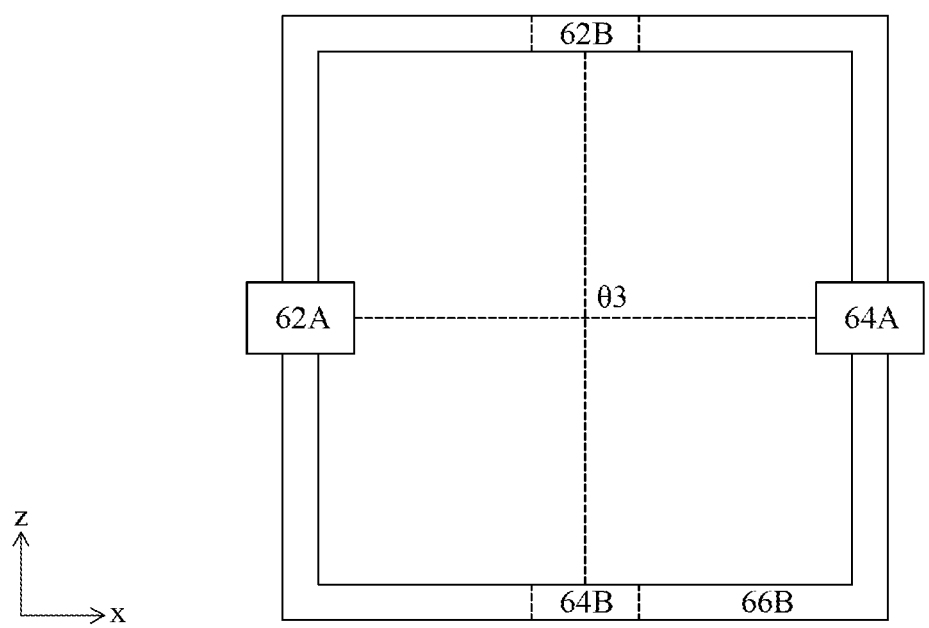
FIG. 9 is a diagram showing the magnetic apparatus of FIG. 6 in an x-z plane in accordance with some embodiments of the present disclosure.

FIG. 9 is a diagram showing the magnetic apparatus 60 of FIG. 6 in an x-z plane in accordance with some embodiments of the present disclosure. Referring to FIG. 9, a plane where the first leg 62A and the second leg 64A are arranged and a plane where the third leg 62B and the fourth leg 64B are arranged has an angle θ3 therebetween. In an embodiment, a plane where the first leg 62A and the second leg 64A are arranged is perpendicular to the plane where the third leg 62B and the fourth leg 64B are arranged. That is, the angle θ3 is 90 degrees. Such arrangement minimizes the size of a magnetic structure (a housing) including the first conductive feature 60A and the second conductive feature 60B. In another embodiment, a plane where the first leg 62A and the second leg 64A are arranged is not perpendicular to the plane where the third leg 62B and the fourth leg 64B are arranged.

Figure 10:
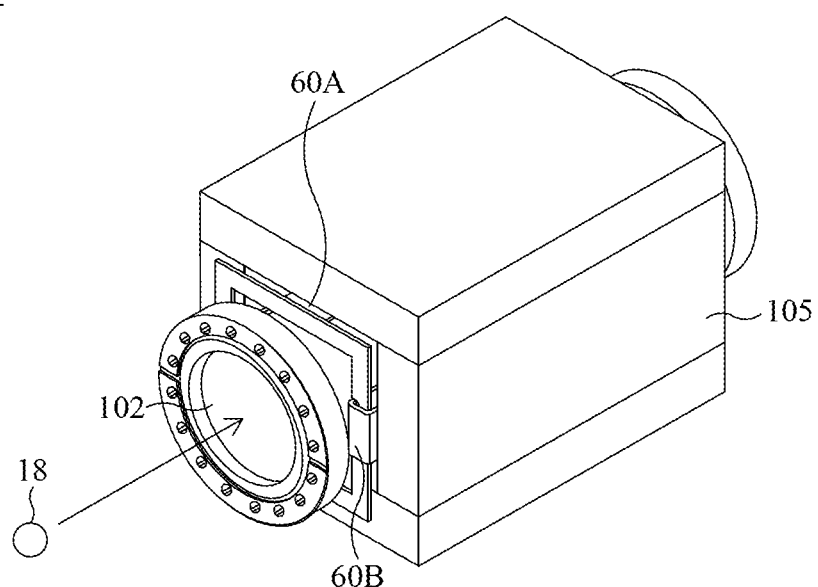
FIG. 10 is a schematic diagram of a magnetic apparatus in accordance with some embodiments of the present disclosure.

FIG. 10 is a schematic diagram of a magnetic apparatus 100 in accordance with some embodiments of the present disclosure. Referring to FIG. 10, the magnetic apparatus 100 includes a device 105 of ferrite materials, and a chamber 102, inside the first conductive feature 60A and the second conductive feature 60B, wherein the electron 18 penetrates the chamber 102. The device 105 functions to uniform a magnetic field in the chamber 102.

Figure 11:
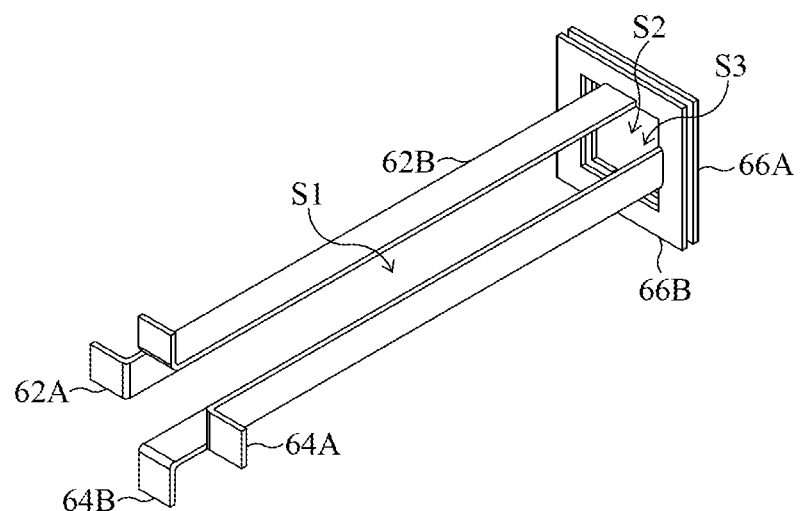
FIG. 11 is a schematic diagram of another magnetic apparatus in accordance with some embodiments of the present disclosure.

FIG. 11 is a schematic diagram of another magnetic apparatus 110 in accordance with some embodiments of the present disclosure. Referring to FIG. 11, the magnetic apparatus 110 is similar to the magnetic apparatus 60 described and illustrated with reference to FIG. 6, except the magnetic apparatus 110 features a different structural arrangement of the first conductive feature 60A and the second conductive feature 60B. The second space S2 defined by the first frame 66A and the third space S3 defined by the second frame 66B are at the same side of the first space S1 defined by the first leg 62A, the second leg 64A, the third leg 66A and the fourth leg 66B.

Figure 12:
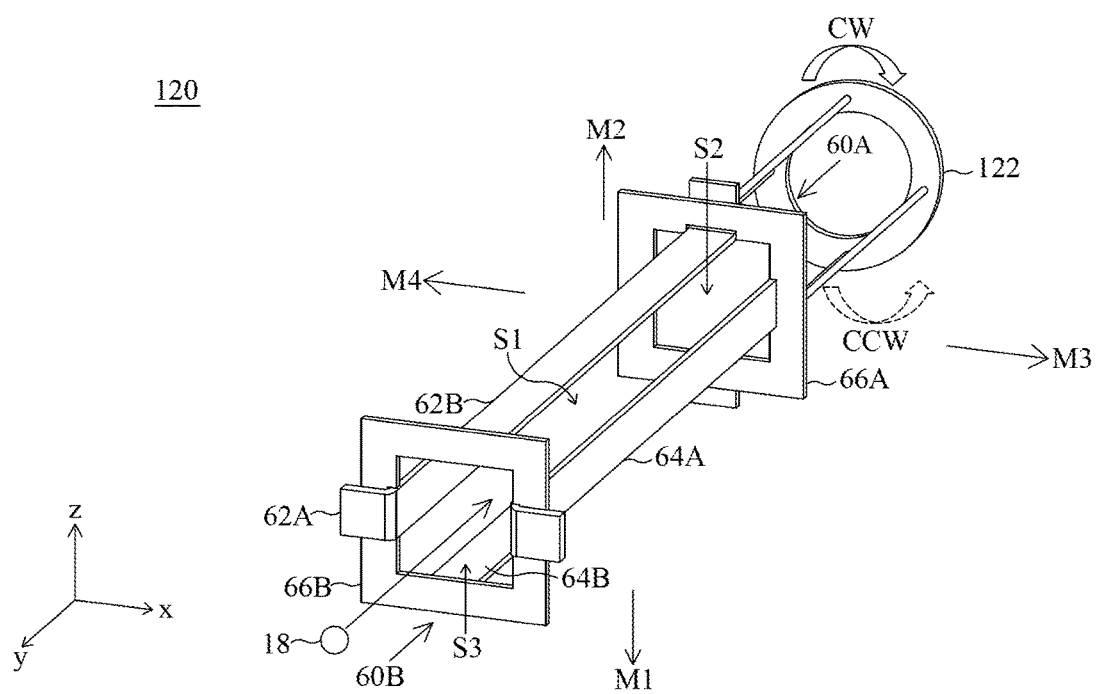
FIG. 12 is a schematic diagram of another magnetic apparatus in accordance with some embodiments of the present disclosure.

FIG. 12 is a schematic diagram of another magnetic apparatus 120 in accordance with some embodiments of the present disclosure. Referring to FIG. 12, the magnetic apparatus 120 is similar to the magnetic apparatus 120 described and illustrated with reference to FIG. 6 except that, the magnetic apparatus 120 includes a rotation feature 122. The rotation feature 122 functions to rotate the first conductive feature 60A and the second conductive feature 60B. In this way, a magnetic field can be accordingly varied. With variation in direction of a magnetic field, a direction of a magnetic force varies. Therefore, the electron 18 can be directed in the first conductive feature 60A and the second conductive feature 60B in all directions (360 degrees) without increasing size of the first conductive feature 60A and the second conductive feature 60B. Moreover, design of the magnetic apparatus 60 including a first conductive feature 60A and a second conductive feature 60B is relatively simple. In an embodiment, the rotation feature 122 is mechanically connected to the first conductive feature 60A and a second conductive feature 60B.

In some related magnetic apparatus, a current with a pulse form (or called a pulsating direct current) is generated and provided to a conductive feature (such as a coil), such that the conductive feature generates a magnetic field to direct an electron having an energy ranging from 50 to 250 MeV. To direct such electron, such that the electron is redirected from its original direction by a relatively large angle, a relatively high magnitude of pulsating current is required. However, pulsating current generally has a relatively low magnitude due to the difficulty in generating high-magnitude pulsating currents. Such resulting low-magnitude pulsating current is only able to redirect the electron by a relatively small angle. To achieve a distance of deviation in an x-axis, a relatively long leg of the conductive feature is required. Consequently, the conductive feature would need to be relatively large.

In contrast, in the present disclosure, a current flowing into a conductive feature has a half-sinewave form and a peak magnitude of the half sinewave is greater than or equal to about, for example, 8000 A (Ampere), wherein a magnitude of 8000 A is a relatively high magnitude. Such resulting high-magnitude current is able to redirect the electron by a relatively large angle. To achieve the same distance of deviation in an x-axis as previously discussed a relatively short leg of the conductive feature is required. Therefore, the size of the conductive feature is relatively small.

Moreover, in the present disclosure, due to the structural arrangement of a first conductive feature and a second conductive feature, an electron can be directed by the simultaneous influence of a first magnetic field and a second magnetic field. Therefore, it is not necessary to have a relatively larger width in an x-axis, for example larger than a width of a first space defined by the first conductive structure and the second conductive structure, to allow sufficient space in an x-axis for the electron to be redirected the desired distance in a z-axis. Accordingly, the width in an x-axis can remain relatively small, allowing the size of a housing containing the first conductive feature and the second conductive feature to also be relatively small. Moreover, in an embodiment, each of the first conductive feature and the second conductive feature can conduct a current with a half-sinewave form, wherein a peak magnitude of the half sinewave is greater than or equal to about, for example, 8000 A. As mentioned above, the length of each of the first conductive feature and the second conductive feature are both relatively short. In this case, the length and the width are both relatively short, and therefore the size of a housing containing the first conductive feature and the second conductive feature is relatively small.

In some related magnetic apparatuses, a first conductive feature and a second conductive feature are separate from each other, and arranged in order in a y-axis. The first conductive feature functions to direct an electron in an x-axis, and the second conductive feature functions to direct the electron in a z-axis. In operation, although the electron leaves from a space defined by the first conductive feature, and enters a space defined by the second conductive feature and therefore the electron is no longer redirected by an magnetic field generated by the first conductive feature, the electron, in the space defined by the second conductive feature, still moves in an x-axis. Because a position in an x-axis is out of a housing, the electron may strike a wall, in an x-axis, of the housing. To ensure proper direction of the electron, therefore, it would require increasing a size of the housing. For example, the housing is enlarged to another housing. Therefore, a size of a housing containing the first conductive feature and the second conductive feature separate from each other need to be relatively large.

In contrast, in the present disclosure, since the first conductive feature and the second conductive feature together define a space in which the electron is redirected, the size of the housing containing the first conductive feature and the second conductive feature is relatively small.

Some embodiments have one or a combination of the following features or advantages. In some embodiments, a magnetic apparatus is provided. The magnetic apparatus includes a first conductive feature. The first conductive feature conducts a current with a half-sinewave form. A peak magnitude of the half sinewave is greater than, for example, 8000 A. The first conductive feature directs an electron having an energy ranging from 50 to 250 MeV in response to a magnetic field generated by the current. The first conductive feature includes a first leg and a second leg. The first leg is integrated with the second leg. The second leg and the first leg define a first space, wherein the electron penetrates the first space and is redirected in the first space.

In some embodiments, a magnetic apparatus is provided. The magnetic apparatus includes a first conductive feature and a second conductive feature. The first conductive feature is configured to generate a first magnetic field. The first conductive feature includes a first leg and a second leg. The second conductive feature is configured to generate a second magnetic field. A direction of the second magnetic field is different from that of the first magnetic field. The first conductive feature and the second conductive feature, electrically isolated from each other, are configured to direct an electron having an energy ranging from 50 to 250 MeV. The second conductive feature includes a third leg and a fourth leg. The first leg, the second leg, the third leg and the fourth leg together define a first space, wherein the electron penetrates the first space and is redirected in the first space.

Although the present disclosure and its advantages have been described in detail, it should be understood that various changes, substitutions and alterations can be made herein without departing from the spirit and scope of the disclosure as defined by the appended claims. For example, many of the processes discussed above can be implemented in different methodologies and replaced by other processes, or a combination thereof.

Moreover, the scope of the present application is not intended to be limited to the particular embodiments of the process, machine, manufacture, and composition of matter, means, methods and steps described in the specification. As one of ordinary skill in the art will readily appreciate from the disclosure of the present disclosure, processes, machines, manufacture, compositions of matter, means, methods, or steps, presently existing or later to be developed, that perform substantially the same function or achieve substantially the same result as the corresponding embodiments described herein may be utilized according to the present disclosure. Accordingly, the appended claims are intended to include within their scope such processes, machines, manufacture, compositions of matter, means, methods, or steps.

What is claimed is:
1. A magnetic apparatus, including:
 a first conductive feature configured to generate a first magnetic field, the first conductive feature including:
  a first leg;
  a second leg separate from the first leg; and
  a first frame configured to connect the first leg to the second leg; and a second conductive feature configured to generate a second magnetic field, wherein a direction of the second magnetic field is different from that of the first magnetic field, the first conductive feature and the second conductive feature, electrically isolated from each other, are configured to direct an electron having an energy ranging from 50 to 250 MeV, and the second conductive feature includes:
a third leg;
a fourth leg separate from the third leg; and
a second frame configured to connect the third leg to the fourth leg, wherein the first leg, the second leg, the third leg and the fourth leg together define a first space,
wherein the electron penetrates the first space and is redirected in the first space,
wherein the first conductive feature is configured to conduct a current, the current flowing from the first leg to the second leg,
wherein each of the first conductive feature and the second conductive feature is configured to conduct a current the first conductive feature generates the first magnetic field in response to the current, and the second conductive feature generates the second magnetic field in response to the current, and
wherein the current is in a half-sinewave form.

2. The magnetic apparatus of claim 1, wherein the first leg is parallel to the second leg, and the third leg is parallel to the fourth leg.

3. The magnetic apparatus of claim 1, wherein the first leg is not parallel to the second leg, and the third leg is not parallel to the fourth leg.

4. The magnetic apparatus of claim 1, wherein the first frame has a second space therein,
wherein the second frame has a third space therein,
wherein the second frame is opposed to the first frame,
wherein the first space, the second space and the third space are connected to each other.

5. The magnetic apparatus of claim 1, wherein each of the first conductive feature and the second conductive feature includes a coil.

6. The magnetic apparatus of claim 5, wherein the coil includes a single-turn coil.

7. The magnetic apparatus of claim 1, wherein each of the first leg and the third leg has a length of 74 cm, which is substantially equal to a distance in the first space at which the electron is directed.

8. The magnetic apparatus of claim 1, wherein a plane where the first leg and the second leg are arranged is perpendicular to the plane where the third leg and the fourth leg are arranged.

9. The magnetic apparatus of claim 1, wherein a plane where the first leg and the second leg are arranged is not perpendicular to a plane where the third leg and the fourth leg are arranged.

10. The magnetic apparatus of claim 1, wherein the first conductive feature further includes a first frame having a second space therein, and the first frame is configured to connect the first leg to the second leg;
wherein the second conductive feature includes a second frame having a third space therein, and the second conductive feature is configured to connect the third leg to the fourth leg, wherein the second space and the third space are at the same side of the first space.

11. The magnetic apparatus of claim 1, wherein the first leg and the second leg are alternately connected to a first node and a second node of a current source.

12. The magnetic apparatus of claim 1, further comprising:
a rotation feature configured to rotate the first conductive feature and the second conductive feature either clockwise or counterclockwise.

13. A magnetic apparatus, comprising:
a first conductive feature configured to conduct a current, and to direct an electron having an energy ranging from 50 to 250 MeV in response to a magnetic field generated by the current, the first conductive feature including:
a first leg;
a second leg separate from the first leg, wherein the second leg and the first leg define a first space; and
a first frame configured to connect the first leg to the second leg,
wherein the electron penetrates the first space and is redirected in the first space,
wherein the first conductive feature is configured to conduct a current, the current flowing from the first leg to the second leg, and
wherein the current is in a half-sinewave form.

14. The magnetic apparatus of claim 13, wherein the first leg is parallel to the second leg.

15. The magnetic apparatus of claim 13, wherein the first leg is not parallel to the second leg.

16. The magnetic apparatus of claim 13, further comprising:
a first frame configured to connect the first leg to the second leg, wherein the first frame has a second space therein, which is connected to the first space, the electron penetrating the second space.

17. The magnetic apparatus of claim 13, wherein the first conductive feature includes a coil.

18. The magnetic apparatus of claim 17, wherein the coil includes a single-turn coil.

19. The magnetic apparatus of claim 17, wherein the first leg has a length of 74 cm, which is substantially equal to a distance in the first space at which the electron is directed.

20. The magnetic apparatus of claim 13, wherein the first conductive feature is rotatable, the magnetic apparatus further comprising:
a rotation feature configured to rotate the first conductive feature either clockwise or counterclockwise.

21. The magnetic apparatus of claim 20, wherein the rotation feature includes a gantry.

* * * * *